United States Patent
Oertig et al.

(10) Patent No.: US 10,160,942 B2
(45) Date of Patent: Dec. 25, 2018

(54) FERMENTER SUPPLY METHOD, BIOGAS PLANT, AND CONVERSION METHOD

(71) Applicant: HITACHI ZOSEN INOVA AG, Zürich (CH)

(72) Inventors: Michael Oertig, Frauenfeld (CH); Rene Leisner, Constance (DE)

(73) Assignee: HITACHI ZOSEN INOVA AG, Zurich (CH)

( * ) Notice: Subject to any disclaimer, the term of this patent is extended or adjusted under 35 U.S.C. 154(b) by 163 days.

(21) Appl. No.: 14/760,955

(22) PCT Filed: Jan. 16, 2014

(86) PCT No.: PCT/EP2014/050817
§ 371 (c)(1),
(2) Date: Jul. 14, 2015

(87) PCT Pub. No.: WO2014/114557
PCT Pub. Date: Jul. 31, 2014

(65) Prior Publication Data
US 2016/0024449 A1    Jan. 28, 2016

(30) Foreign Application Priority Data
Jan. 25, 2013  (CH) ........................................ 300/13

(51) Int. Cl.
| C12M 1/107 | (2006.01) |
| C12M 1/00 | (2006.01) |
| C12P 5/02 | (2006.01) |

(52) U.S. Cl.
CPC ............ *C12M 21/04* (2013.01); *C12M 23/58* (2013.01); *C12M 29/18* (2013.01); *C12P 5/023* (2013.01); *Y02E 50/343* (2013.01)

(58) Field of Classification Search
None
See application file for complete search history.

(56) References Cited

U.S. PATENT DOCUMENTS

| 5,514,278 A * | 5/1996 | Khudenko | ............. C02F 3/006 |
| | | | 210/605 |
| 5,601,720 A | 2/1997 | Schmid | |
| 8,592,191 B2 * | 11/2013 | Bell | ......................... C12N 1/20 |
| | | | 435/140 |

FOREIGN PATENT DOCUMENTS

| EP | 0 621 336 A2 | 10/1994 |
| EP | 1 930 404 A1 | 6/2008 |
| GB | 720 018 A | 12/1954 |
| WO | 2006/079228 A1 | 8/2006 |
| WO | 2013/002949 A1 | 1/2013 |

OTHER PUBLICATIONS

May 21, 2015 Search Report issued in International Patent Application No. PCT/EP2014/050817.
Jul. 28, 2015 International Preliminary Report on Patentability issued in International Patent Application No. PCT/EP2014/050817.

* cited by examiner

Primary Examiner — Vera Afremova
(74) Attorney, Agent, or Firm — Oliff PLC

(57) ABSTRACT

A biogas plant fermenter supply method increases total throughput of substrate through fermenter chambers while not changing the number of fermenter chambers. An inoculum fermenter chamber is supplied with raw fermentation substrate and fermenting for a dwell time, returning part of the substrate fermented in the inoculum fermenter chamber in the form of a self-inoculating substrate to the inoculum fermenter chamber by a return path, the part being mixed with the raw fermentation substrate, and supplying a fast fermenter chamber coupled to the inoculum fermenter chamber with an additional part of the substrate fermented in the inoculum fermenter chamber in the form of a fast fermenter inoculation substrate and mixing the additional part with fast fermenter raw substrate of an amount per unit of time, wherein fermented output substrate is removed from the fast fermenter chamber after a dwell time of the substrate mixture introduced into the fast fermenter chamber.

6 Claims, 1 Drawing Sheet prior art

FERMENTER SUPPLY METHOD, BIOGAS PLANT, AND CONVERSION METHOD

TECHNICAL FIELD

The present invention relates to a fermenter supply method for a biogas plant, to a biogas plant comprising a plurality of fermenter chambers, and to a conversion method for a biogas plant having at least one fermenter chamber.

STATE OF THE ART

Several different embodiments of fermenters of anaerobic fermentation of biomass in biogas plants are known.

The applicant is aware of horizontal fermenters operated in plug-flow mode that are suitable for anaerobic fermentation of biogenic wastes and operate according to the method of European patent EP 0 621 336. The fermenter is an elongated, horizontal tank having in inlet at one end and an outlet at the opposite end. The chopped biogenic wastes are supplied through the inlet and are inoculated by means of fermented material and press water from the conditioning. By this, the substrate to be fermented is enriched with methanobacteria. In the fermenter, the biogenic wastes are now decomposed under controlled mixing forming biogas, and are subsequently, after exiting through the outlet, supplied to aerobic rotting.

The worldwide demand for plants of the kind described at the outset having ever larger capacities leads to the construction of increasingly large fermenters. This requires that the fermenters are built on-site as fermenter tanks from steel or concrete. In order to increase capacity, horizontal fermenter tanks of a total length of 50 meters and more are realized nowadays, having a diameter of more than 10 meters. A stirring unit operated in such a tank not only needs to mix the biogenic wastes in order to achieve a certain homogeneity, but at the same time also needs to prevent the sedimentation of heavy solids, such as in particular sand and stones, at the bottom of the fermenter tanks, which would no longer be discharged. Even though the fermenter is operated in plug-flow mode, the perfusion is not capable of discharging the sinking heavy goods because the plug-flow has only low flow velocity. The passing time of the biogenic wastes through the fermenter from the inlet to the outlet is several days.

Consequently, apart from the mixing, the stirring unit also helps to move these heavy goods from the bottom towards the top again, such that during the subsequent sinking they are moved in the direction of the fermenter outlet by the plug-flow. For this reason, the stirring unit of a shaft crossing the fermenter comprises a multitude of agitating arms, which are provided with suitable blades at their ends away from the shaft.

The technical difficulties associated with the transport of the fermentation substrate through the fermenter, as well as with the control of the fermentation process by measuring and optimizing parameters like temperature, water content of the fermentation substrate and pH value, have been solved. Also the realization of fermentation methods allowing for conserving the fermenter parts, is known from EP 1 841 853, for example.

In order to increase the overall throughput of the fermenter substrate through the biogas plant, the dwell time of the fermenter substrate in the fermenter can be reduced, as disclosed in EP 1 930 404. EP 1 930 404 discloses a fermentation method, wherein partially fermented inoculation substrate from an outlet of the fermenter is returned into the same fermenter and used as an inoculation means. Thereby, the use of the partially fermented inoculation substrate from the fermenter itself is used for self-inoculation of the fresh biomass in the inlet area of the fermenter. In this way, the throughput through the single fermenter can be increased and the dwell time reduce to a few days.

The overall biomass throughput of a biogas plant can thus be increased by a plurality of fermenters operated according to EP 1 930 404, which are operated in parallel to each other. The maximal throughput thus achievable therefore corresponds to the number of fermenters multiplied by the throughput of each fermenter. This is shown as an example in FIG. 2. In this case, the discharge from both fermenters is doubled, while the dwell time of the biomass in the fermenters is the same and part of the discharge of each fermenter is used for self-inoculation of said fermenter.

GB 720,018 does not rely on classic self-inoculation. GB 720,018 discloses an anaerobic fermentation method for biomass, wherein several fermenter chambers are used, through which the fermentation substrate is fed in a predetermined order. There is no indication that the throughput of biomass through the biogas plant could or should be increased by the method according to GB 720,018. The digester liquor formed upon fermentation in the fast fermenter is supplied to the separate inoculation fermenter, such that bacteria may be reused in the inoculation fermenter. It is not disclosed and also not recognizable to the person skilled in the art if this procedure leads to an increased throughput. This measure does not allow for a reuse of the bacteria, which would lead to an optimization of the operational procedure and to a certain reduction of costs. The idea of the self-inoculation according to EP 1 930 404 teaches away from the idea of returning the digester liquor formed in the fast fermenter from the fast fermenter to the separate inoculation fermenter according to GB 720,018, such that a combination of the two methods is not suggested and the person skilled in the art is lead away from a combination.

DESCRIPTION OF THE INVENTION

The present invention has the intention to provide a method by which the total throughput of the substrate through a plurality of fermenter chambers in a biogas plant is increased, wherein the number of fermenter chambers is not changed. By means of a minimal instrumental effort, an overall throughput through the biogas plant of more than the n-times throughput of each separate fermenter chamber can be achieved.

Even though a plurality of fermenter chambers is used, the necessary investments in equipment technology compared to the achievable overall throughput is smaller than for simple parallel arrangement of n non-coupled fermenter chambers.

This problem is solved by a special supply and coupling of the plurality of fermenter chambers. Thanks to the fact that self-inoculating substrate from an inoculum fermenter chamber is returned to the inoculum fermenter chamber by means of a return path and in addition is supplied to at least one further fast fermenter chamber independent from the inoculum fermenter chamber by means of a fast inoculation path and is mixed there with additional fresh raw fermentation substrate. This allows for achieving a significantly shorter dwell time in the fast fermenter chamber and for increasing the overall throughput of raw fermentation substrate of the biogas plant comparted to a biogas plant having the same number of fermenter chambers operated in parallel.

BRIEF DESCRIPTION OF DRAWINGS

A preferred embodiment of the present invention will be described in connection with the enclosed drawings.

DESCRIPTION

This application discloses several fermenter chambers in the form of closed rooms, which may be separated from each other in space or arranged adjacent to each other. The pertaining interior spaces are separated from each other and are coupled with each other by means of different conduits or paths.

Figure 1:
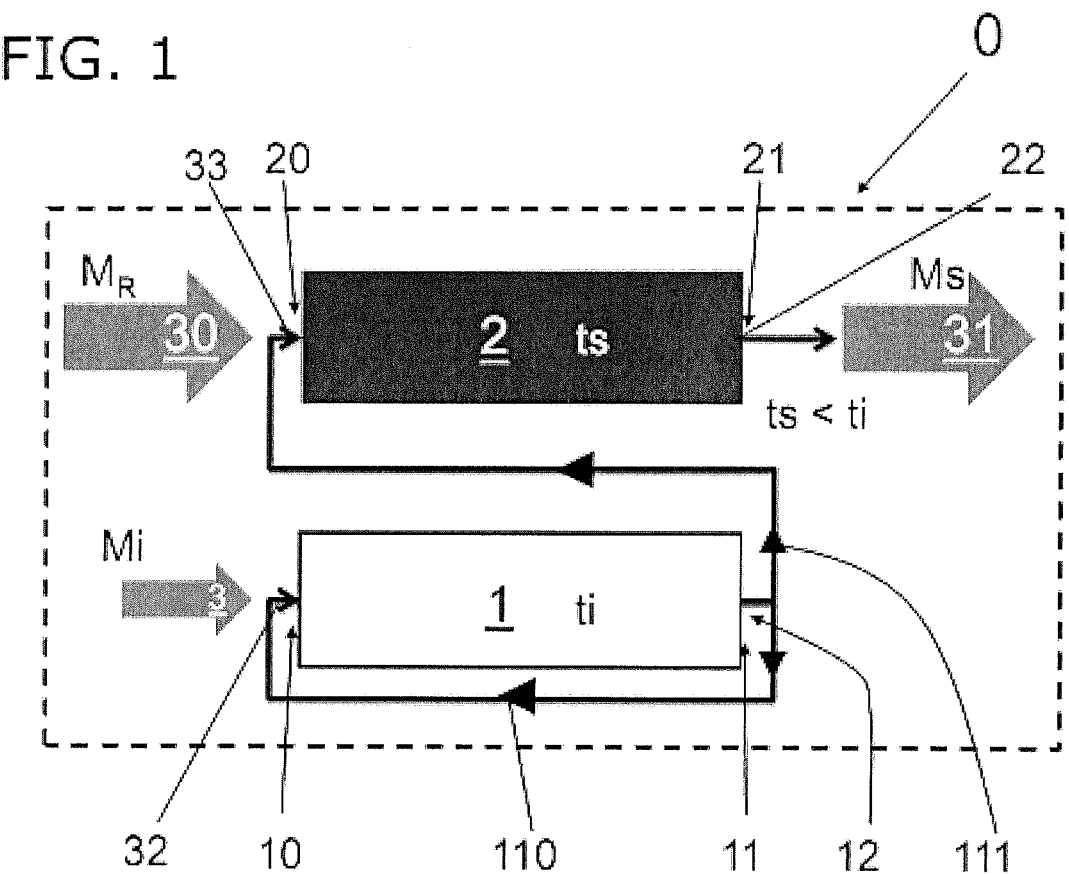
FIG. 1 shows a schematic view of a biogas plant having an inoculation fermenter chamber and a fast fermenter chamber, which are coupled to each other and are supplied with substrate according to the method of the present invention.
Figure 2:
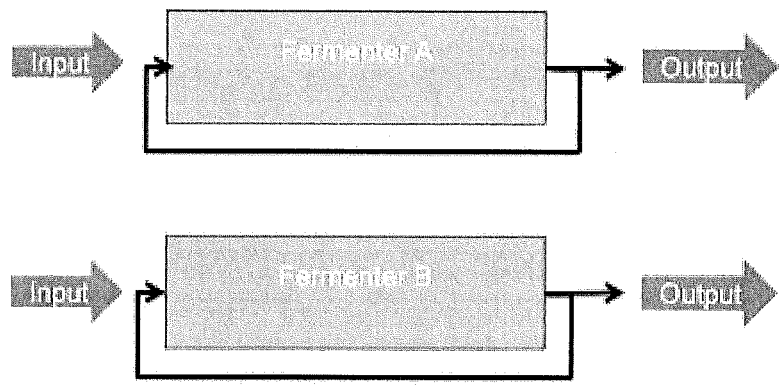
FIG. 2 shows a schematic view of a first and a second fermenter with self-inoculation, which are operated in parallel, according to the state of the art.

FIG. 1 shows a biogas plant 0 comprising, as an example, an inoculation fermenter chamber 1 and a fast fermenter chamber 2 coupled to the inoculation fermenter chamber 1. In the biogas plant 0 shown here, both fermenter chambers have an identical size of interior space and thus also identical effective volumes, which may be loaded or supplied with fermentation substrate. The biogas plant 0 may optionally have several inoculation fermenter chambers and/or several fast fermenter chambers 2, which are coupled and supplied as follows.

The method is also applicable to fermenter chambers having different effective volumes, but will be exemplified here with respect to identical effective volumes.

From the input side 10, the inoculation fermenter chamber 1 is supplied with raw fermentation substrate 3, which is furthered in the plug-flow mode towards the output side 11 of the inoculation fermenter chamber 1. The raw fermentation substrate 3 is fermented in the inoculation fermenter chamber 1 within a dwell time ti of a few days, until fermented inoculation fermenter substrate results.

From an outlet at the output side 11, self-inoculating substrate 32 which is part of the fermented inoculation fermenter substrate, is returned to the input side 10 of the inoculum fermenter chamber 1 by means of a return path 110 and is reintroduced into the interior room of the inoculum fermenter chamber 1. Thereby, the self-inoculating substrate 32 is mixed with fresh raw fermentation substrate 3 to form a substrate mixture. Said substrate mixture is subsequently fermented upon passing the inoculum fermenter chamber 1 in the plug-flow mode. Thus, the supply of the inoculum fermenter chamber 1 effected by means of a self-inoculation of fresh raw fermentation substrate with fermented self-inoculating substrate 32 from the inoculum fermenter chamber 1. Overall, the inoculum fermenter chamber 1 is supplied with an amount Mi of raw fermentation substrate 3 per unit of time, which forms part of the overall throughput amount Ms of the biogas plant 0 per unit of time.

An addition part of the substrate fermented in the inoculum fermenter chamber 1, which is designated as fast fermenter inoculation substrate 33, is supplied from the outlet 12 via a fast fermentation path 111 to the input side 20 of the fast fermenter chamber 2. There, the fast fermenter inoculation substrate 33 is introduced into the fast fermenter chamber 2 together with an amount MR of fast fermenter raw substrate 30, such that an inoculation of the fresh fast fermenter raw substrate 30 takes place in the fast fermenter chamber 2. The mixture of fast fermenter inoculation substrate 33 and fresh fast fermenter raw substrate 30 is also furthered through the fast fermenter chamber 2 and to an outlet side 21 by means of plug-flow and thereby fermented. After a dwell time is in the fast fermenter chamber 2, fermented output substrate 31 is removed via an outlet 22. Overall, a total amount Ms of fermented substrate is passed through the biogas plant 0 and fermented. This total amount Ms per unit of time is correlated to the sum of the amount Mi of raw fermentation substrate passing through the inoculation fermenter chamber and the amount MR of the fast fermenter raw substrate, wherein Ms is smaller than the sum of Mi+MR, since about 10% of the mas is transformed to biogas.

According to the supply method presented here, both fermenter chambers 1, 2 are supplied with different amounts Mi, MR of raw fermentation substrate. This is possible because the fermentation in the fast fermenter chamber 2 proceeds significantly faster than that in the inoculation fermenter chamber 1, since the fast fermenter chamber 2 does not inoculate itself. Because the fast fermenter chamber 2 does not need to inoculate itself, the dwell time ts in the fast fermenter chamber 2 can be substantially reduced. Consequently, the dwell time ti of the substrate in the inoculation fermenter chamber 1 is longer than the dwell time ts of the substrate in the fast fermenter chamber 2.

This leads to almost a doubling of the amount MR of fast fermenter raw substrate per unit of time and thus of the fast fermenter throughput, and the overall throughput of the biogas plant 0 can be significantly increased in comparison to the operation of two identical fermenter chambers operated in parallel.

The buildup of such a biogas plant 0 requires only one return path 110 per inoculation fermenter chamber 1, wherein fermented output substrate 31 can be directly removed from the outlet side 21 of the fast fermenter chamber 2 for further use.

It has been found that, by using an inoculation fermenter chamber 1 having a throughput Mi of 20000 Mg/a and an identical fast fermenter chamber 2 having a throughput of 35000 Mg/a, an overall throughput of 55000 Mg/a can be achieved. By operating the fermenter chambers according to the classical method of self-inoculation, an overall throughput of only 40000 Mg/a is achievable, since each fermenter relying on self-inoculation has an identical throughput of 20000 Mg/a.

The gas output of a biogas plant 0 according to FIG. 1 is, however, slightly lower than that of two fermenter chambers operated in parallel. The reason for this is the in comparison shorter dwelling time is in the fast fermenter chamber 2.

For comparison of the supply method of the present invention with the state of the art, table 1 contrasts two biogas plants. In an embodiment according to the state of the art, three identical fermenter chambers are operated in parallel, reaching an overall annual throughput of all three fermenter chambers of 60000 megagram per year. Each of the fermenter chambers is operated independently from the others and provides one third of the overall annual throughput.

In a biogas plant having an inoculation fermenter chamber and a fast fermenter chamber, upon operation according to the supply method of the present invention, an overall annual throughput of 55000 megagram per year can be reached even when using one fermenter chamber less.

TABLE 1

| State of the Art Construction | | Fast Fermenter Construction | |
|---|---|---|---|
| 60'000 Mg/a | Throughput | 55'000 Mg/a | |
| 3 | Number of fermenter chambers | 2 | |
| 6.285 Mio Nm³/a | Gas output | 5.395 Mio Nm³/a | |
| 105 Nm³/Mg | Special gas output | 98 Nm³/Mg | |

In a test plant, two fermenter chambers 1, 2 having identical effective volumes were coupled and supplied with substrates. The supply parameters used and the technical details of the fermenter chambers 1, 2 are listed in table 2.

TABLE 2

| Inoculum Fermenter | | Fast Fermenter | |
|---|---|---|---|
| Limit Values: | | Limit Values: | |
| Spec gas prod | 4.42 Nm³/m³ (max 4.5) | Spec gas prod | 6.95 Nm³/m³ (max 4.5) |
| Spec gas prod | 6.05 Bm³/m³ (max 6.5) | Spec gas prod | 9.53 Bm³/m³ (max 6.5) |
| Loading | 11.0 kgoTS/m³·d (max 10) | Loading | 19.2 kgoTS/m³·d (max 10) |
| Loading | 6.0 kgoTS/m³·d (max 6.5) | Loading | 10.5 kgoTS/m³·d (max 6.5) |
| Med dwell time | 18.9 d | Med dwell time | 10.8 d |
| Hydr pass time | 12.6 d | Hydr pass time | 7.2 d |
| Fermenter | GG20Modul | Fermenter | GG20Modul |
| Fermenter number | 1 | Fermenter number | 1 |
| Fermenter effective volume | 1300 m³ | Fermenter effective volume | 1300 m³ |
| Output | | Output | |
| Spec gas production | 105 Nm³/t sm | Spec gas production | 94 Nm³/t sm |
| Spec gas production | 262 Nm³/t sm | Spec gas production | 236 Nm³/t sm |
| Spec gas production | 403 Nm³/t sm | Spec gas production | 363 Nm³/t sm |
| Gas volume stream | 20951000 Nm³/a | Gas volume stream | 33001000 Nm³/a |
| Gas volume stream | 5740 mNm³/d and fermenter | Gas volume stream | 9040 mNm³/d and fermenter |

Apart from the depicted spaced apart arrangement of the inoculation fermenter chamber 1 and the fast fermenter chamber 2, these may also be arranged directly neighboring with very short paths 110, 111 or may be directly adjacent each other, such that a compact biogas plant 0 may be built.

Preferably, one inoculation fermenter chamber 1 coupled to two or three fast fermenter chambers 2 is provided. This allows for providing sufficient fast fermenter inoculation substrate 33 to optimize operation of the plurality of fast fermenter chambers 2.

It is possible to convert existing biogas plants having at least one fermenter chamber such that they may be operated according to the herein described fermenter supply method. To this end, at least one inoculation fermenter chamber 1 has to be equipped with a return path 110 and operatively coupled to at least one fast fermenter chamber 2 by means of a fast inoculation path 111. Such a conversion method is advisable in order to increase the raw substrate throughput through a biogas plant. Since known biogas plants, in many cases, comprises a plurality of separate fermenter chambers operated in parallel, the conversion method consists of coupling the fast fermenter chamber 2 and the inoculation fermenter chamber 1.

LIST OF REFERENCE SIGNS

0 Biogas plant
1 Inoculation fermenter chamber
  10 Input side
  11 Output side
    110 Return path
    111 Fast inoculation path
  12 Outlet
2 Fast fermenter chamber
  20 Input side
  21 Output side
  22 Outlet
3 Raw fermentation substrate
  30 Fast fermenter raw substrate
  31 Fermented output substrate
  32 Self-inoculating substrate
  33 Fast fermenter inoculation substrate
ti Dwelling time in inoculation fermenter chamber
ts Dwelling time in fast fermenter chamber
Mi Amount through inoculation fermenter chamber per unit of time/inoculation throughput
MR Amount of fast fermenter raw substrate per unit of time/fast fermenter throughput
Ms Overall amount through biogas plant per unit of time/overall throughput

The invention claimed is:
1. A fermenter supply method for a biogas plant, the method comprising:
supplying at least one inoculum fermenter chamber with raw fermentation substrate of an amount per unit of time and fermenting for a dwell time;
returning part of the substrate fermented in the inoculum fermenter chamber, which is a self-inoculating substrate, directly to the inoculum fermenter chamber by way of a return path that leads directly from the at least one inoculum fermenter chamber back to the at least one inoculum fermenter chamber, the returned substrate being mixed with further raw fermentation substrate; and
supplying, by way of a fast fermentation path that is separate from the return path, at least one fast fermenter chamber coupled to the inoculum fermenter chamber with an additional part of the substrate fermented in the inoculum fermenter chamber, which is a fast fermenter inoculation substrate, and mixing the additional substrate with fast fermenter raw substrate of an amount per unit of time, wherein:
fermented output substrate is removed from the fast fermenter chamber after a dwell time of the substrate mixture introduced into the fast fermenter chamber,
the composition of the returned substrate is the same as that which leaves the inoculum fermenter chamber, and
the at least inoculum fermenter chamber and the at least one fast fermenter chamber are operated in plug-flow mode.

2. The fermenter supply method according to claim 1, wherein the dwell time in the fast fermenter chamber is shorter than the dwell time in the inoculum fermenter chamber.

3. The fermenter supply method according to claim 1, wherein the amount of the raw fermentation substrate, with which the inoculum fermenter chamber is supplied per unit of time, is smaller than the amount of the fast fermenter raw substrate per unit of time, with which the fast fermenter chamber is supplied.

4. The fermenter supply method according to claim 1, wherein at any time the returned substrate is returned to the inoculum fermenter chamber and the additional substrate is supplied to the fast fermenter chamber.

5. The fermenter supply method according to claim 1, wherein the at least one inoculum fermenter chamber is coupled to more than one of the fast fermenter chambers.

6. The fermenter supply method according to claim 1, wherein the return path directly leads from the at least one inoculum fermenter chamber back to the at least one inoculum fermenter chamber without any further treatment of the self-inoculating substrate.

\* \* \* \* \*